US00PP33254P2

(12) United States Plant Patent
Verhoef

(10) Patent No.: US PP33,254 P2
(45) Date of Patent: Jul. 13, 2021

(54) ***WEIGELA* PLANT NAMED 'AZ'**

(50) Latin Name: ***Weigela* hybrid**
Varietal Denomination: AZ

(71) Applicant: Gijsbertus Verhoef, Hazerswoude-Dorp (NL)

(72) Inventor: Gijsbertus Verhoef, Hazerswoude-Dorp (NL)

(73) Assignee: BERT VERHOEF BOOMKWEKERIJ B.V., Hazerswoude-Dorp (NL)

( * ) Notice: Subject to any disclaimer, the term of this patent is extended or adjusted under 35 U.S.C. 154(b) by 0 days.

(21) Appl. No.: 17/000,691

(22) Filed: Aug. 24, 2020

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Weigela* named 'AZ' that is characterized by its dense and compact plant habit, its flowers that are light grey-purple in color, its young foliage that is grey-purple to brown in color, and its floriferous blooming habit.

2 Drawing Sheets

Botanical classification: *Weigela* hybrid.
Variety denomination: 'AZ'.

BACKGROUND OF THE INVENTION

The present invention relates to a new and distinct cultivar of *Weigela* of hybrid origin and will be referred to hereafter by its cultivar name, 'AZ'. 'AZ' represents a new cultivar of *Weigela*, a deciduous shrub grown for landscape use.

'AZ' was discovered by the Inventor as a chance seedling in a field plot that had been planted with seed collected from numerous open pollinated unnamed and named plants of *Weigela* in Hazerswoude-Dorp, The Netherlands in June of 2014. The parentage is unknown.

Asexual propagation of the new cultivar was first accomplished by softwood stem cuttings by the Inventor in July of 2015 in Hazerswoude-Dorp, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'AZ' as a unique cultivar of *Weigela*.

1. 'AZ' exhibits a dense and compact plant habit.
2. 'AZ' exhibits flowers that are light grey-purple in color.
3. 'AZ' exhibits young foliage that is grey-purple to brown in color.
4. 'AZ' exhibits a floriferous blooming habit.

'AZ' can be most closely compared to the *Weigela florida* 'Velda' (U.S. Plant Pat. No. 26,842) and *Weigela* hybrid 'Courtacad1' (U.S. Plant Pat. No. 22,766). 'Velda' and 'Courtacad1' are both similar to 'AZ' in having a compact plant habit. 'Velda' and 'Courtacad1' both differ from 'AZ' in having foliage that is darker in color, flowers that are whiter in color, and being taller in height.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure include but may not be limited to website and facebook postings by Blooming Easy and listed in a plant database by The National Gardening Association.

BRIEF DESCRIPTION OF THE DRAWINGS

The accompanying colored photographs illustrates the overall appearance and distinct characteristics of the new *Weigela*. The photographs were taken of a six-year-old plant as grown outdoors in a trial field in Hazerswoude-Dorp, The Netherlands. The plants had been pruned (back to 10 cm) in early spring (3 months prior to the description).

The photograph in FIG. 1 provides an overall view of the growth habit of 'AZ'.

Figure 1:
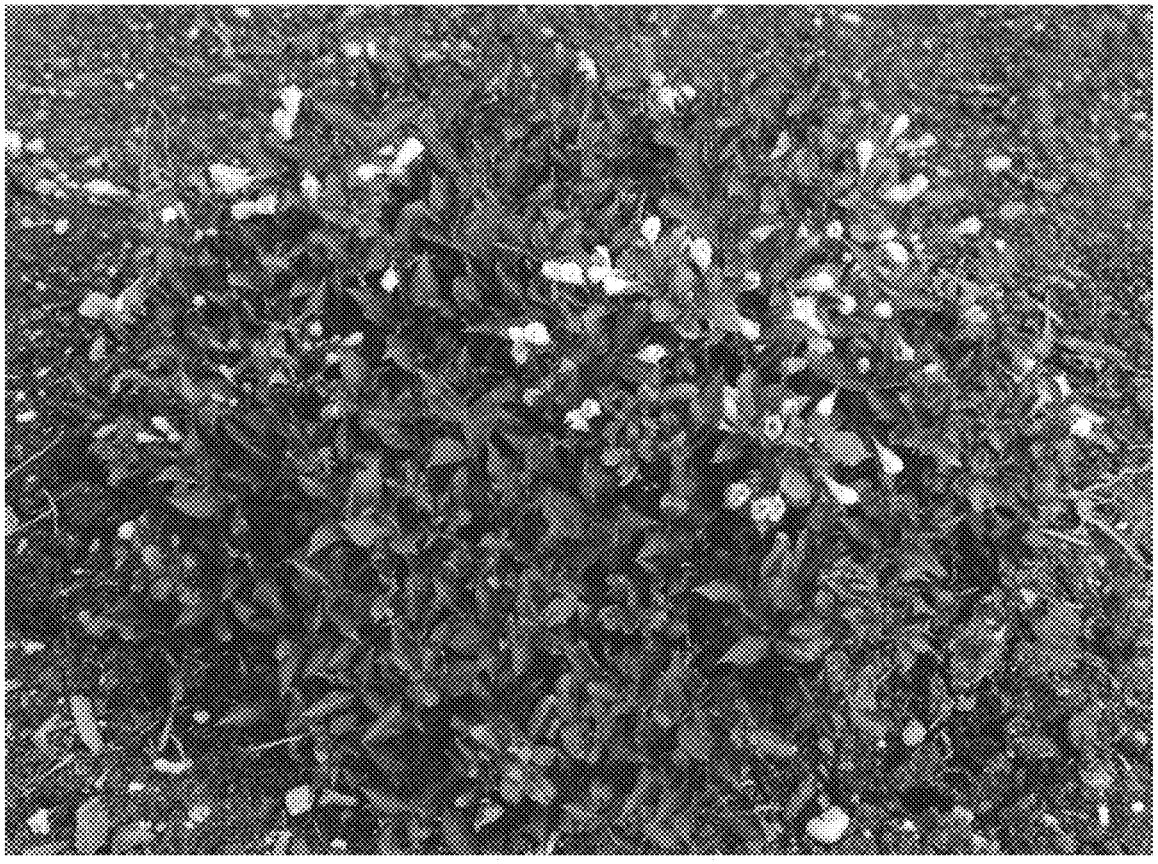
Figure 2:
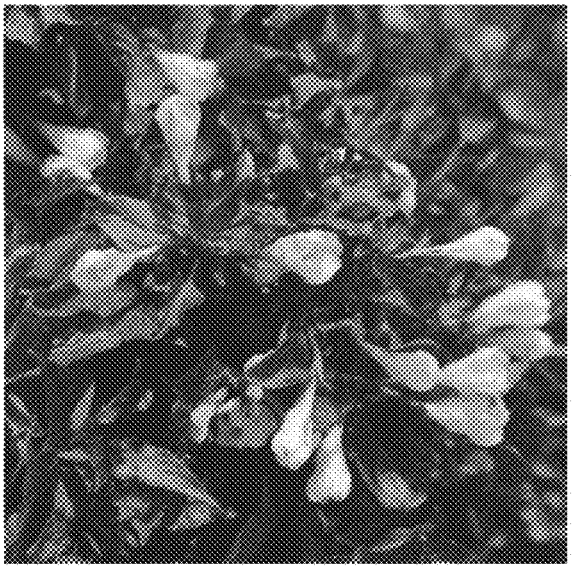

The photograph in FIG. 2 provides a close-up view of the flowers of 'AZ'.

Figure 3:
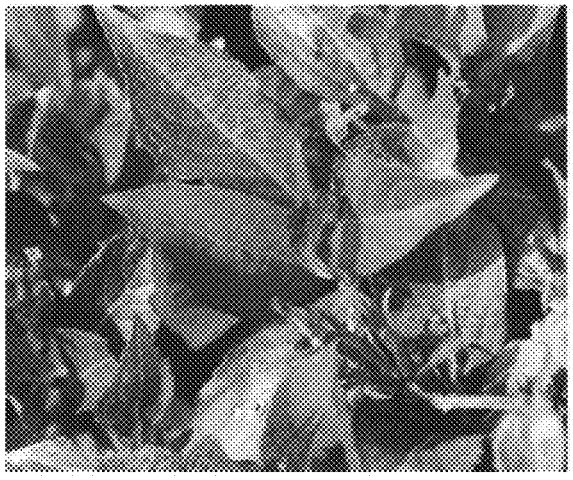

The photograph in FIG. 3 provides a close-up view of the maturing foliage of 'AZ'.

Figure 4:
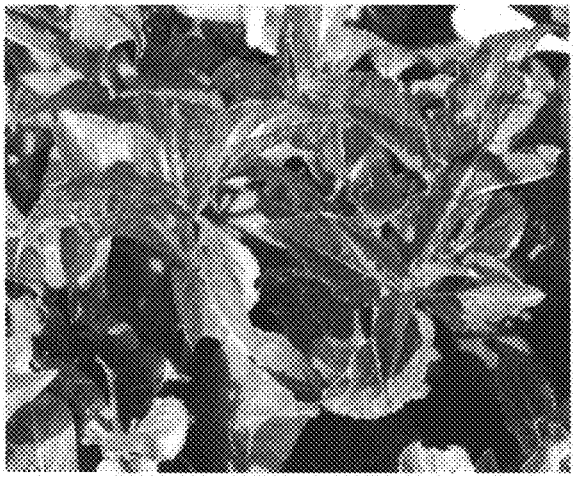

The photograph in FIG. 4 provides a close-up view of the young foliage of 'AZ'.

The colors in the photographs may differ slightly from the color values cited in the detailed botanical description, which accurately describe the colors of the new *Weigela*.

DETAILED BOTANICAL DESCRIPTION

The following is a detailed description of six-year-old plants as grown outdoors in a trial field in Hazerswoude-Dorp, The Netherlands. The plants had been pruned (back to 10 cm) in early spring (3 months prior to the description). Phenotypic differences may be observed with variations in environmental, climatic, and cultural conditions. The color determination is in accordance with The 2015 Colour Chart of The Royal Horticultural Society, London, England, except where general color terms of ordinary dictionary significance are used.

General description:

*Blooming period*.—Blooms in late spring (May and June) with some repeat flowering in early fall (late August to mid-September) in The Netherlands.

*Plant type*.—Deciduous shrub.

*Plant habit*.—Compact, broadly spreading to broadly spreading-upright.

*Plant size*.—An average of 20.1 cm in height (soil level to top of foliar plane) and 31 cm in diameter as a 6-year old plant in June after a hard prune in March, reaches about 80 cm in height and 100 cm in width as a mature plant in the landscape.

*Hardiness*.—At least in U.S.D.A. Zones 5 to 9.

*Diseases and pests*.—No susceptibility to resistance to diseases or pests has been observed.

*Root description*.—Fibrous, moderately dense.

*Propagation*.—Softwood stem cuttings.

*Root initiation*.—An average of 6 weeks.

*Root development*.—An average of 3 months to produce a young rooted plant.

*Growth rate*.—Moderately vigorous.

Branch description:

*Branch shape*.—Circular, very slightly quadrangular.

*Branch color*.—New growth; between N186C and 200B, lower side 152A, mature stems; 195A, flushed 183A and 183B, old wood; 199C and 199D.

*Branch size*.—An average of 13.4 cm in length and 3 mm in diameter.

*Branch surface*.—Slightly glossy, angles of stems moderately to densely covered with short adpressed hairs average of 0.75 mm in length, 156D in color.

*Branch aspect*.—Upright to outward at an average angle of 45°.

*Branch quantity*.—Average of 132 main branches, 2.6 lateral branches per main stem, very freely branching.

*Internode length*.—Average of 3.6 cm.

Foliage description:

*Leaf shape*.—Ovate to obovate.

*Leaf division*.—Simple.

*Leaf base*.—Short acute.

*Leaf apex*.—Apiculate.

*Leaf fragrance*.—None.

*Leaf venation*.—Pinnate, color upper surface; 148B to 148C, lower surface 146D.

*Leaf margins*.—Serrate.

*Leaf arrangement*.—Opposite.

*Leaf attachment*.—Petiolate.

*Leaf surface*.—Both surfaces are smooth, rugose and moderately covered with very short hairs an average of 0.75 mm in length and 156B in color.

*Leaf size*.—An average of 4.2 cm in length and 2.3 cm in width.

*Leaf quantity*.—An average of 8 (4 pairs) per lateral branch.

*Leaf color*.—Young upper and lower surface; between N186C and 200B, mature and fall upper surface; 146B, mature and fall lower surface; 147B, tinged 200C.

*Petioles*.—Average of 3.5 mm in length, 1.5 mm in width, flattened, upper and lower surface color 146D, both surfaces and margins moderately to densely pubescent with soft hairs and average of 0.75 mm in length and 156A in color.

*Stipules*.—None.

Inflorescence description:

*Inflorescence type*.—Terminal raceme.

*Inflorescence size*.—3.4 cm in height (including peduncle), 4.3 cm in diameter.

*Flower buds*.—Oblanceolate in shape, an average of 2.7 cm in depth and 6 mm in diameter, 150D, changing darker towards the top to 150C to 150B, base changing to 187B, surface is smooth, glabrous and matte.

*Flower fragrance*.—None.

*Lastingness of flowers*.—About 12 days, self-cleaning.

*Flower aspect*.—Outward to slightly upright.

*Flower quantity*.—An average 7 per inflorescence, 100 flowers per plant, 400 buds per plant.

*Flower type*.—Narrow campanulate, single.

*Flower size*.—Average of 1.2 cm in height and diameter, 3.7 cm in depth, throat; 8 mm in diameter, tube; 2.1 cm in length, 6 mm in diameter.

*Peduncles*.—Average of 4 mm in length and 1.25 mm in diameter, held in a 20° angle to lateral branch, strong, 138B in color, matte and sparsely pubescent covered with soft hairs an average of 5 mm in length, NN155D in color.

*Calyx*.—Rotate in shape, an average of 7 mm in depth and width.

*Sepals*.—5, rotate, linear in shape, narrowly acute apex, cuneate base fused, entire margin, an average of 7 mm in length and 1 cm in width, upper and lower surface is smooth and glabrous, color; when opening upper and lower surface between 148A and N199A, when fully open upper and lower surface 177A and 177B.

*Petals*.—5, whorled, lower 75% fused into tube, spathulate in shape, margin entire on free portion, apex obtuse, an average of 2.7 cm in length, 8 mm in width, upper and lower surface glabrous and matte, color; when opening upper surface 155A, one petal has a macule that is 31B, when opening lower surface N155B, slightly flushed with 185D at the margins, when fully open upper surface N155B, strongly tinged 186C at the margins, one petal has a macule 35B, throat 186C, tube 186C changing to 180A at the base, when fully open lower surface N155A, strongly tinged 186B at the margins, throat 186C, tube 182C to 182D.

Reproductive organs:

*Gynoecium*.—Pistil; 1, average of 2.1 cm in length, style; average of 2 cm in length, 147D, changing to 186D at the base in color, stigma; club-shaped, 1 mm in length, 1.5 mm in diameter, 147D in color, ovary; 147B in color.

*Androecium*.—Stamens; 5, filaments; 186D, changing to 186C in color and an average of 6 mm in length, anthers; 158D in color, an average of 3 mm in length, 0.5 mm in width, narrowly oblong in shape, pollen; moderate to high in quantity and 155C in color.

*Fruit and seed*.—No fruit or seed production has been observed to date.

It is claimed:

1. A new and distinct cultivar of *Weigela* plant named 'AZ' as herein illustrated and described.

* * * * *